United States Patent
Hernandez et al.

(10) Patent No.: US 6,235,795 B1
(45) Date of Patent: *May 22, 2001

(54) NATURAL MIXTURE COMPOSED OF HIGHER PRIMARY ALIPHATIC ALCOHOLS OBTAINED FROM BEE WAX FOR THE TREATMENT OF GASTRIC AND DUODENAL ULCERS THAT ALSO PRESENT ANTIINFLAMATORY ACTIVITY

(75) Inventors: Juan Magraner Hernandez; Abilio Laguna Granja; Rosa Mas Ferreiro; Maria de Lourdes Arruzazabala Valmaña; Daysi Carvajal Quintana; Vivian Molina Sánchez; Suria Valdés García; Maritza Díaz Gómez, all of Cuidad de La Habana (CU)

(73) Assignee: Laboratorios Dalmer SA (CU)

( * ) Notice: Subject to any disclaimer, the term of this patent is extended or adjusted under 35 U.S.C. 154(b) by 0 days.

This patent is subject to a terminal disclaimer.

(21) Appl. No.: 08/335,300

(22) Filed: Nov. 7, 1994

(30) Foreign Application Priority Data

Nov. 9, 1993 (CU) ........................................ 101/93

(51) Int. Cl.⁷ .................. A61K 31/045; A61K 47/00
(52) U.S. Cl. .......................... 514/724; 514/787; 514/925
(58) Field of Search ..................... 514/787, 724, 514/925

(56) References Cited

U.S. PATENT DOCUMENTS

| 4,738,956 | * | 4/1988 | Scott ..................................... 514/179 |
| 5,296,514 | * | 3/1994 | Muller ................................. 514/724 |

\* cited by examiner

Primary Examiner—T J Criares
(74) Attorney, Agent, or Firm—Gottlieb, Rackman & Reisman, P.C.

(57) ABSTRACT

This invention is related with the obtention of a new natural mixture composed by higher primary aliphatic alcohols, eventually in an extended range of 22 to 38 carbon atoms, specially those between 24 and 34 carbon atoms and more specially those of 24, 26, 28, 30, 32 and 34 carbon atoms. This mixture shows a relative composition of each alcohol that is highly reproducible from batch to batch and is obtained from bee wax.

This natural mixture has been used, with efficacy, as an active principle, in different pharmaceutical formulations used against ulcer, and/or protector of the gastric and duodenal mucose, and shows antiinflamatory activity administered by topical, oral or parenteral route.

1 Claim, No Drawings

NATURAL MIXTURE COMPOSED OF HIGHER PRIMARY ALIPHATIC ALCOHOLS OBTAINED FROM BEE WAX FOR THE TREATMENT OF GASTRIC AND DUODENAL ULCERS THAT ALSO PRESENT ANTIINFLAMATORY ACTIVITY

INTRODUCTION

This invention is related with the obtention of a new natural mixture composed by higher aliphatic primary alcohols eventually in an extended range of 22 to 38 carbon atoms, specially those between 24 and 34 carbon atoms and more specially those of 24, 26, 28, 30, 32 and 34 carbon atoms. This mixture shows a relative composition of each alcohol that is highly reproducible from batch to batch.

The present invention is related, mainly, with the pharmaceutical industry and particularly with the development of pharmaceuticals formulations with specific properties, because they can be used against gastric and duodenal ulcers as well as an antiinflamatory agents.

These formulations contains, as active ingredient, a natural mixture of higher primary aliphatic alcohols of lineal chain, from 24 to 34 carbon atoms, especially those of 24, 26, 28, 30, 32 and 34 carbon atoms obtained from bee wax (M.H.A.A.B.W. in the rest of the text).

Drugs with specific pharmacological properties, based in the use, as an active ingredient of this higher primary aliphatic alcohols saturated of lineal chain from 24 to 34 carbon atoms are not reported with frequency, only the natural mixture obtained from sugar cane wax (EPA 0 488 928) has been reported previously.

The utilization of products produced by bee in empiric medicine is known since before our Era. With the development of new methods of analysis it was posbile to identify, in many cases, the active principles present in these products, that has permited to understood some biological and pharmacodynamics effects of them. Among these products, with therapeutics properties, can be signaled the royal jelly, honey, pollen and bee wax. This last one is generally used in the pharmaceutical and cosmetics industries taking into account their nutritives, cleaning and other medicinal properties as well as it possibilities to be used as false face for skin. Bee wax is mainly composed by the following type of compounds:

saturated and unsaturated long chain hydrocarbons (55–75%) from 21 to 37 carbon atoms fatty esthers (aproximately 30%), that contains lineal alcohols of long chains (from 16 to 30 carbon atoms)

free fatty acids (aproximately 1–5%) in a range between 16 to 30 carbon atoms, also the 18:1 acid that represents 30% of the acidic fraction.

free alcohols of long chain (aproximately 1–7%), being triacontanol, octacosanol and hexacosanol the most abundant ones.

other polar constituents (aproximately 1–3%).

The procedure of the current invention is based on a homogeneous phase saponification process of the bee wax, previously melted, with concentrated solutions of alkaline and alkaline terrum hydroxides, especially those of low molecular weight and more especially with those of sodium, potassium and calcium.

The concentration of the hydroxide solutions must be such that the ratio in weight of the corresponding hydroxide with that of the bee wax to be processed must be over 5% on, specially from 8 to 25% and more specially, from 15 to 25%. The saponification process remains for a period of 30 minutes on and more specially from 2 to 5 hours.

The solid, obtained in this step, is taken to a solid-liquid extractor, where M.H.A.A.B.W. is selectively extracted with adequate organic solvents, choosen among ketones from 3 to 8 carbon atoms, hydrocarbons from 6 to 9 carbon atoms, alcohols from 1 to 5 carbon atoms, haloforms as well as aromatic compounds such as benzene and it derivatives, including mixtures of them. Some of the solvents used in the present invention are the following: acetone, methyl ethyl ketone, pentanone, hexanone, heptanone, 2 methylpentanone, ethanol, methanol, 2-propanol, butanol, terbutanol, pentane, hexane, heptane, octane, chloroform, 1,2 dichloroethane, dichloromethane, trichloroethane, 1,2,3 trichloropropane, benzene, toluene, phenol, p-methyl toluene and others.

The extraction is carried out in periods ranging between 5 up to 10 hours. Afterwards, the product is successively crystallized using the above mentioned solvents or their mixtures. The yield attained ranges about 30%, while the purity of the product (M.H.A.A.B.W.) is in a attained ranges from 80 to 98% and more especially between 90 and 98%.

The product (M.H.A.A.B.W.) thus obtained in the present invention is a mixture composed by higher primary aliphatic alcohols ranging between 24 to 34 carbon atoms. It shows a fusion point between 80.0 and 82.5° C. The proposed procedure for obtaining M.H.A.A.B.W. from bee wax has some advantages with regards to other previously reported. One of these advantages is related with the short obtention time. Other advantage of this invention is related with the practical yields of M.H.A.A.B.W. obtained (near 30% in weight) compared with other results previously described. Other advantage of the proposed procedure is related with the purity degree of the obtained product, the one that is significantly higher than that of other works previously reported. In Table 1 is reported the more general qualitative and quantitative composition of the M.H.A.A.B.W. and in Table 2 is reported the qualitative and quantitative composition of the M.H.A.A.B.W.

TABLE 1

General qualitative and quantitative composition of M.H.A.A.B.W. obtained

| Component | Percent in the mixture |
|---|---|
| 1-tetracosanol | 9.0–15.0% |
| 1-hexacosanol | 12.0–18.0% |
| 1-octacosanol | 13.0–20.0% |
| 1-triacontanol | 20.0–30.0% |
| 1-dotriacontanol | 13.0–21.0% |
| 1-tetratriacontanol | 1.5–3.5% |

TABLE 2

Specific qualitative and quantitative composition of M.H.A.A.B.W. obtained

| Component | Percent in the mixture |
|---|---|
| 1-tetracosanol | 12.5 +/− 1.0% |
| 1-hexacosanol | 14.5 +/− 1.2% |
| 1-octacosanol | 16.5 +/− 2.0% |
| 1-triacontanol | 24.6 +/− 1.6% |
| 1-dotriacontanol | 16.7 +/− 1.4% |
| 1-tetratriacontanol | 2.3 +/− 0.5% |

The daily dosage of M.H.A.A.B.W. to be used for treatment of different diseases has been established between 1 to 100 mg per day and the most adequate route of administration is oral, in form of tablets as well as granules or capsules. Although, this drug can be administered parenterally or topically, taking into account the uses that are recomended in the present invention.

The pharmaceutical formulation contains as an active ingredient from 0.5 to 25.0% wt of M.H.A.A.B.W. This dosage is obtained by mixing this M.H.A.A.B.W. with different excipients, such as agglutinants, disintegrators, lubricants, sliders or just fillers. In these excipients are included lactose, corn starch, saccharose, magnesium stearate, microcrystalline cellulose, sodium croscarmellose gelatin, cellulose acetophtalate, titanium dioxide, special talc for tablets, polyethylenglycol, polivinylpirrolidone and others.

One of the objectives of this invention is to obtain, isolate and purify the natural mixture composed by higher primary aliphatic alcohols in the range from 24 to 34 carbon atoms starting from the bee wax, specifically the one that contains the primary alcohols of 24, 26, 28, 30, 32 and 34 carbon atoms.

Other objective of this invention is to use those natural mixture, at relatively low doses, as a component of the pharmaceutical formulation in drugs used against gastric and duodenal ulcers. Proving that this new M.H.A.A.B.W. reduce significantly the gastric ulcers induced by aspirin, ethanol, indomethacine and other related drugs that are able to produced gastric ulcers in patients under treatment. Also, this M.H.A.A.B.W. reduce significantly the duodenal ulcers.

Other of the objectives of the present invention is the development of pharmaceutical formulations, that contains M.H.A.A.B.W. as active ingredient, to be used as antiinflamatory drugs, both administered by oral, topic of parenteral route.

Finally, a global valoration of this M.H.A.A.B.W. obtained in the present invention and proposed to be used as an active ingredient and drug formulations, can concluded that it is a very safety and well tolerated mixture, that represents an important advantage. This can be sustented by the results obtained in acute, subchronic and chronic toxicity assays developed in rodents and rabbits that reported no drug-related toxicity. Moreover, it does not show any mutagenic effect nor has teratogenic effects in rodents. No colateral effects has been detected in human being under clinical trials treated with the product object of the present invention.

The purpose of the current invention shall be described in detail as follows. References made to implementation examples shall not be limited to the scope of said invention.

EXAMPLE 1

1,000g of refined bee wax are taken, melted at 100–110° C., adding 200 g of potassium hydroxide dissolved in 150 ml of water. This saponification process is mantained for 30 minutes with periodic stirring. To the obtained solid the M.H.A.A.B.W. is extracted by extracting it with heptane, in a solid-liquid extracting system. Then, the extract is cooled at room temperature and crystallized in methyl ethyl ketone. There where obtained 250 g of M.H.A.A.B.W. with a purity of 93.26%. The melting point of the mixture range between 81.0 and 82.5° C. Table 3 shows the qualitative and quantitative composition of M.H.A.A.B.W. obtained using this procedure.

TABLE 3

Qualitative and quantitative composition of M.H.A.A.B.W. obtained

| Component | Percentage of each alcohol |
| --- | --- |
| 1 - tetracosanol | 13.21 |
| 1 - hexacosanol | 15.50 |
| 1 - octacosanol | 17.89 |
| 1 - triacontanol | 26.03 |
| 1 - dotriacontanol | 18.05 |
| 1 - tetratriacontanol | 2.58 |

EXAMPLE 2

Two (2) kg of bee wax are taken to be melted at 90–100° C., to which 300 g of sodium hydroxide dissolved in 200 mL of water are added. The saponification process remains for a period of 3 hours with stirring. M.H.A.A.B.W. is extracted with ethanol for a period of 12 hours in a conventional solid-liquid extraction system. The extract obtained is cooled at room temperature and the solid obtain is recrystallized in methanol. 393 g of M.H.A.A.B.W. were obtain with a purity amounting to 93.32%. The melting point of the mixture ranges from 80.5–82.0° C. In Table 4 is shown the gualitative and quantitative composition of the obtained M.H.A.A.B.W.

TABLE 4

Qualitative and quantitative composition of M.H.A.A.B.W. obtained

| Component | Percentage of each alcohol |
| --- | --- |
| 1 - tetracosanol | 13.28 |
| 1 - hexacosanol | 15.42 |
| 1 - octacosanol | 18.11 |
| 1 - triacontanol | 26.10 |
| 1 - dotriacontanol | 17.73 |
| 1 - tetratriacontanol | 2.68 |

EXAMPLE 3

Fifty (50) kg of bee wax are taken and melted at 100–120° C. After that are added 12 kg of calcium hydroxide dissolved in 10 L of water. The saponification process is continued for 3.5 hours with stirring M.H.A.A.B.W. is extracted with chloroform as solvent for 12 in a solid-liquid extractor with adequate capacity. The product obtained is left to cool at room temperature and later on is recrystallized in heptane, there were obtained 14.5 kg of the M.H.A.A.B.W. with a purity of 93.77%. The melting point ranges from 81.5–82.5° C. In Table 5 is shown the qualitative and quantitative composition of the M.H.A.A.B.W. obtained by this procedure.

TABLE 5

Qualitative and quantitative composition of M.H.A.A.B.W. obtained

| Component | Percentage of each alcohol |
| --- | --- |
| 1 - tetracosanol | 13.48 |
| 1 - hexacosanol | 16.12 |

TABLE 5-continued

Qualitative and quantitative composition of M.H.A.A.B.W. obtained

| Component | Percentage of each alcohol |
|---|---|
| 1 - octacosanol | 17.51 |
| 1 - triacontanol | 26.55 |
| 1 - dotriacontanol | 17.73 |
| 1 - tetratriacontanol | 2.38 |

EXAMPLE 4

Fifty (50) kg of bee wax are melted at 100–120° C. and 10.6 kg of sodium hydroxide dissolved in 7.5 L of ethanol/water 1/1 are added. The saponification process is continued for 4.5 hours with continous stirring M.H.A.A.B.W. is extracted with 2-propanol for 12 h in a solid-liquid extractor. The product is left to cool at room temperature and the solid obtained is recrystallized in a mixture of toluen:chloroform 1:1. 9.3 kg of M.H.A.A.B.W. were obtained with a purity of 93.36% determined by gas chromatography. The melting point range from 80.5–82.0° C. In Table 6 is shown the qualitative and quantitative composition of the M.H.A.A.B.W. obtained.

TABLE 6

Qualitative and quantitative composition of M.H.A.A.B.W. obtained.

| Component | Percentage of each alcohol |
|---|---|
| 1 - tetracosanol | 13.33 |
| 1 - hexacosanol | 15.54 |
| 1 - octacosanol | 17.02 |
| 1 - triacontanol | 27.04 |
| 1 - dotriacontanol | 17.83 |
| 1 - tetratriacontanol | 2.60 |

EXAMPLE 5

Two different pharmaceutical formulations, using this M.H.A.A.B.W. as active principle, were developed. The composition of each formulation is shown in Table 7. These formulations were developed taking into account the physical, chemical and physico-chemical characteristics of the M.H.A.A.B.W.

TABLE 6

Pharmaceutical formulations using M.H.A.A.B.W. as active principle

| Component | Formulation 1 (%) | Formulation 2 (%) |
|---|---|---|
| M.H.A.A.B.W. | 5.0 | 15.0 |
| Lactose | 56.5 | 55.0 |
| Corn Starch | 15.0 | 10.0 |
| Polivinyl pirrolidone | 2.5 | 2.0 |
| Sodium Croscarmellose | 5.0 | 4.0 |
| Saccharose | 5.0 | 4.0 |
| Talc | 2.0 | 2.0 |
| Magnesium stearate | 1.5 | 1.0 |
| Microcrystalline Cellulose | 7.5 | 7.0 |

EXAMPLE 6

Female Sprague Dawley rats, weighing 200 to 250 g and male Hartley guinea pigs, weighing 300 to 400 g, were adapted to laboratory conditions for 7 days. Rats were divided randomly in different experimental groups. After a 24 h fast period, one group was intraperitoneally injected with M.H.A.A.B.W. suspended in a 20% Tween 20/water vehicle, while the controls only received the same volume of vehicle (Tween 20/water). These treatments were administered 1 h before the induction of the ulcer. The agent used as inductor of ulcer were: NaOH (0.2 mol/L), alcohol (60%), ASA (40 mg/kg) and indomethacine (50 mg/kg) (indomethacine was dissolved in 5% sodium bicarbonate) and then where administred by gastric gavage.

Induced by alcohol: One h after dosing vehicle or M.H.A.A.B.W. 1, 5, 25, 50 and 100 mg/kg, each rat was administered orally with ethanol 60% (1 mL/200 g) by gastric gavage. One h later, rats were sacrificed and the quantification of gastric ulcer was performed.

Induced by ASA: Guinea pigs were distributed in 4 experimental groups, one control group and 3 groups treated with M.H.A.A.B.W. (5, 25 and 100 mg/kg), the animals were i.p. injected. The control group received equivalent volume of the vehicle, One hour later, rats were administered gastrically with ASA (40 mg/kg) and 2 h later, rats were sacrificed and the procedure for gastric ulcer measurement was done.

Induced by indomethacine: Rats were divided randomly into 3 experimental groups: a control group and 2 groups treated with M.H.A.A.B.W. at 25 and 50 mg/kg, administered i.p. One hour later, indomethacine was administered by gastric gavage and 4 h later the animals were sacrificed and the quantification of gastric ulcer was performed. In all cases, when ulcer are induced, inmediately after sacrificed, the stomach were removed and opened by the bigger curvature, washed with saline solution and measured the size of the ulcer. Results were expressed as the sumatory of the lessions in milimiters, the lessions were measured always by 2 different observers.

In all cases, the comparison between the treated groups and the control one was realized using the non parametric U de Mann Whitney test. The results of the effect of the M.H.A.A.B.W. over the gastric ulcer induced by alcohol, ASA and indomethacine are shown in Table 8, 9 and 10 respectively.

TABLE 8

Effect of M.H.A.A.B.W. over the gastric ulcer induced by alcohol (60%)

| Treatment | Dose (mg/kg) | n | (X +/− DE) Size of the ulcer (mm) |
|---|---|---|---|
| Control | | 25 | 35.46 +/− 4.81 |
| M.H.A.A.B.W. | 1 | 10 | 35.28 +/− 9.13 |
| | 5 | 10 | 4.11 +/− 1.57*** |
| | 25 | 10 | 8.90 +/− 3.82*** |
| | 100 | 10 | 9.35 +/− 3.88** | p << 0.01; *p << 0.001 (U de Mann Whitney test)

TABLE 9

Effect of M.H.A.A.B.W. over the gastric ulcer induced by ASA (40 mg/kg)

| Treatment | Dose (mg/kg) | n | (X +/− ES) Size of the ulcer (mm) |
|---|---|---|---|
| Control | | 8 | 39.37 +/− 10.69 |
| M.H.A.A.B.W. | 5 | 6 | 38.00 +/− 13.90 |

TABLE 9-continued

Effect of M.H.A.A.B.W. over the gastric ulcer induced by ASA (40 mg/kg)

| Treatment | Dose (mg/kg) | n | (X +/- ES) Size of the ulcer (mm) |
|---|---|---|---|
| | 25 | 8 | 9.50 +/- 1.72* |
| | 100 | 6 | 25.83 +/- 3.77 |

*p << 0.05 (U de Mann Whitney test)

TABLE 10

Effect of M.H.A.A.B.W. over the gastric ulcer induced by indomethacine (50 mg/kg)

| Treatment | Dose (mg/kg) | n | (X +/- ES) Size of the ulcer (mm) |
|---|---|---|---|
| Control | | 11 | 38.65 +/- 9.48 |
| M.H.A.A.B.W. | 25 | 11 | 17.50 +/- 4.38* |
| | 50 | 10 | 13.14 +/- 3.60* |

*p << 0.05 (U de Mann Whitney test)

The M.H.A.A.B.W. protect the gastric mucose in the models of ulcer induced by alcohol, ASA and indomethacine (Table 8, 9 and 10), diminishing significantly the size of the ulcer.

EXAMPLE 7

The objective of the present work is to determine if the protective effect of M.H.A.A.B.W. against ulcer is dependent of prostaglandins or not. Male Sprague Dawley rats, weighing 150 to 200 g, were adapted to laboratory conditions for 7 days with water and food ad libitum, up to 48 h previous to the experiment, where food is suppressed. The animals were randomly distributed in 4 experimental groups.

M.H.A.A.B.W. was administered intraperitoneally in a 2% Tween 20/water suspension, cimetidine was dissolved in hot water and indomethacine in 5% sodium bicarbonate. The four experimetnal groups are the following (n=10):1) control (vehicle); 2 and 3) M.H.A.A.B.W. at 25 and 50 mg/kg respectively and 4) cimetidine 25 mg/kg. Inmediately after the animals were injected by i.p. route indomethacine was administered at 10 mg/kg by subcutaneous route. Half an hour later, was administered 60% alcohol and, an hour later, the animals were sacrificed. The stomachs were extracted, opened by the bigger curvature and measured the size of the ulcer using a 3x enlargement. Results were expressed in milimiters.

In all cases, the comparison between the treated groups and the control one was realized using the non parametric U de Mann Whitney test. The results of the effect of the M.H.A.A.B.W. over the gastric ulcer induced by alcohol and indomethacine are shown in Table 11.

TABLE 11

Effect of M.H.A.A.B.W. ver the gastric ulcer induced by alcohol (60%) and indometacine (10 mg/kg)

| Treatment | Dose (mg/kg) | n | Ulcer (mm) | Inhibition (%) |
|---|---|---|---|---|
| Alcohol 60% | | 10 | 35.3 + 2.95 | |
| Indometacine | | 10 | 0 | |
| Indometacine + alcohol + tween | | 9 | 54.6 +/- 8.55 | |
| M.H.A.A.B.W. | 25 | 8 | 13.8 +/- 5.44* | 72.8 |
| | 50 | 5 | 18.0 +/- 6.04* | 64.5 |
| Cimetidine | 25 | 9 | 14.6 +/- 5.64* | 71.2 |

*p << 0.05 (U de Mann Whitney test)

As it can be observed from the Table, both when M.H.A.A.B.W. or cimetidine are used, the ulcer induced by alcohol, at the evaluated doses, are diminished, also, with the previous administratiuon of indomethacine. This one, alone do not produce ulcer and potentiated the ulcer effect of alcohol.

The experimental design is based on the administration of indomethacine previous to the induction of the ulcer by alcohol, while if the compound mantains the protective affect against ulcer it will be independent of prostaglandins, that indicates that the effect agaisnt ulcers of M.H.A.A.B.W. is mantained in spite of the administration of indomethacine, it is possible to outline that this protective effect could be independent of prostaglandins.

EXAMPLE 8

The results obtained in last examples sugest an action over ulcer induced by acid compounds dependent or independent. With the objective of discard the inhibitory effect over the inhibition of the acid gastric secretion was determined the action of M.H.A.A.B.W. over this acid gastric secretion in the pilorous ligature model.

Female Sprague Dawley rats, weighing 150 to 200 g were adapted to laboratory conditions for 15 days with water and food ad libitum. The animals were randomly distributed in different experimental groups and food was deprived 48 h previous to the ligature. M.H.A.A.B.W. was administered intraperitoneally in a 2% Tween 20/water suspension.

Cimetidine was dissolved in hot water and administered by the same route as M.H.A.A.B.W. Animals were divided in 6 experimetnal groups: 1) control (vehicle); 2, 3 and 4) M.H.A.A.B.W. at 25, 50 and 100 mg/kg respectively and 5 and 6) (positive control) cimetidine at 25 and 50 mg/kg respectively.

Rats were anaesthetized with ether and an incision, in the abdominal region was done, stomachs were extracted and pilorous were ligatured with thread. Inmediately, after that, the compound was administered by i.p. route and 3 mL of saline solution were injected by subcutaneous route. Four h later, the animals were sacrificed, intact stomachs were extracted, tweezed by the esophagus. The gastric content was centrifuged at 3000 $min^{-1}$ for 10 min and, later on, the volume was measured. The acidity of the gastric juice was measured using 0.1 mol/L NaOH and phenolphtalein as indicator. The comparison between the treated groups and the control one was realized using the non parametric U de Mann Whitney test. The results of the effect of the M.H.A.A.B.W. over the gastric acidity in the pilorous ligature are shown in Table 12.

TABLE 12

Effect of la M.H.A.A.B.W. over the gastric acidity in the model of pilorous ligatured

| Treatment | Dose (mg/kg) | n | Gastric juice volume (mL) | Acidity (meq H$^+$/mL) |
|---|---|---|---|---|
| Control | | 12 | 8.18 +/− 0.51 | 0.109 +/− 0.002 |
| M.H.A.A.B.W. | 25 | 10 | 5.00 +/− 0.58* | 0.09 +/− 0.01 |
| | 50 | 11 | 5.51 +/− 0.54* | 0.104 +/− 0.006 |
| | 100 | 10 | 5.49 +/− 0.65* | 0.114 +/− 0.002 |
| Cimetidine | 25 | 9 | 5.87 +/− 0.63* | 0.080 +/− 0.009* |
| | 50 | 9 | 5.83 +/− 0.38** | 0.083 +/− 0.006** |

*p << 0.05; **p << 0.01 (U de Mann Whitney test)

As it can be observed, when M.H.A.A.B.W. (25, 50 and 100 mg/kg) is administered the volume of gastric juice in the rats with pilorous ligatured is reduced significantly, the maximun effect is obtained with the lower dose (25 mg/kg). Cimetidine at 25 and 50 mg/kg significatively reduced, both, the volume of gastric juice as well as the concentration of H$^+$ iones.

In this assay is demonstrated that M.H.A.A.B.W. (25, 50 and 100 mg/kg) significatively inhibited the volume of gastric juice in the pilorous ligature-model without affecting the content of H$^+$ ions, fact that, practically, discarded an antisecretor effect of H$^+$ ions as cimetidine or omeprazol type.

EXAMPLE 9

In order to corroborate the antiinflamatory effect of the M.H.A.A.B.W. are used the pleuresy induced by carragenine and the granule by cotton models, those ones that constitute established models for the evaluation of antiinflamatory drugs.

Granule by cotton: Male Sprague Dawley rats, weighing 200 to 250 g, were adapted to laboratory conditions in the same way as the last experiment. M.H.A.A.B.W. was administered orally in a 2% Tween 20/water suspension, while indomethacine was dissolved in 5% sodium bicarbonate. Both treatments were administered by gastric gavage during 6 days after the implantation of cotton. Rats were randomly distributed in 5 experimental groups: 1) control (vehicle); 2, 3, and 4) M.H.A.A.B.W. at 25, 50 and 100 mg/kg respectively and 5) indomethacine at 3 mg/kg. Rats were, previously, anaesthetized with ether, doing an incision in the dorsal region. The esterile cotton pellet of 50 mg was sub-cutaneously and applied with a local anaesthesic and finally the injured is closed.

One day after the last administration of the products the animals were sacrificed in ether atmosphere and the granules were carefully dissected and dried in an oven at 60° C. for 24 h, the dry weight were determined. The weight of the cotton pellet (50 mg) was deducted from the weight of the granule. The percent of inhibition was expressed taking as reference the weight of the granule formed in the control group. The results of the M.H.A.A.B.W. over the cotton granule are shown in Table 13.

TABLE 13

Effect of the administration of M.H.A.A.B.W. over the model of cotton granule

| Treatment | Dose (mg/kg) | n | Weight of granule (mg) | Inhibition (%) |
|---|---|---|---|---|
| Control | | 8 | 258 + 0.12 | |
| M.H.A.A.B.W | 25 | 8 | 138 + 0.05* | 46.51 |
| | 50 | 7 | 162 + 0.11** | 54.7 |
| | 100 | 9 | 117 + 0.04** | 54.7 |
| Indometacine | 3 | 5 | 79 + 0.02** | 69.3 |

*p < 0.05, **p < 0.01 (U de Mann Whitney test)

As can be observed in the Table, M.H.A.A.B.W. significantly reduced the weight of the cotton granule when it was administered in a range of 25 to 100 mg/kg, the maximun answer was observed at the lower dose (25 mg/kg). Although, in none of the used doses is observed a 100% of the reduction of the inflamation.

Pleuresy by carragenine: Male Sprague Dawley rats were used (200–250 g) and adapted to laboratory conditions for 15 days with water and food ad libitum and were deprived of food 12 h previous to the experiment. M.H.A.A.B.W. was administered in a 10 mg/mL acacia gum/water suspension, as well as triacontanol, while indomethacine was dissolved in 5% sodium bicarbonate.

All the treatments were administered using gastric gavage one hour previous to the injection of carragenine. Rats were randomly distributed in the following experimental groups: 1) control (vehicle); 2, 3 and 4) M.H.A.A.B.W. at 25, 50 and 100 mg/kg respectively; 5) triacontanol at 50 mg/kg and 6) indomethacine at 10 mg/kg.

For the induction of the edema, rats were anesthesized with ether and 0.3 mL of carragenine in 1% of saline solution were injected in the pleural cavity. Five hours later, the animals were sacrificed and the exudate were colected, determining its volume. The percent of inhibition of the edema is calculated using the following formula:

Inhibition (%)=1−(VT)/(VC)×100 where:
VT=volume of the edema of treated animals
VC=volume of the edema of control animals
The results of this experiments are shown in Table 14.

TABLE 14

Effect of the oral administration of M.H.A.A.B.W. in the pleuresy induced by carragenine

| Treatment | Dose (mg/kg) | n | Exudate volume (mL) | Inhibition (%) |
|---|---|---|---|---|
| Control | | 15 | 1.24 + 0.30 | |
| M.H.A.A.B.W. | 25 | 10 | 1.13 + 0.39 | 8.9 |
| | 50 | 10 | 0.98 + 0.36 | 20.9 |
| | 100 | 11 | 0.85 + 0.28* | 31.4 |
| Triacontanol | 100 | 10 | 0.96 + 0.30* | 27.4 |
| Indometacine | 10 | 14 | 0.50 + 0.15*** | 59.6 |

*p < 0.05 ***p < 0.001 (U de Mann Whitney test)

As can be observed in the Table, the M.H.A.A.B.W., at the maximum dose assayed, shows a moderated antiinflamatory effect, inhibiting the volume of pleural exudate in a 23.3%, being this one, the maximun observed effect, while indomethacine (10 mg/kg) produce a protective effectivity of the edema with 59.6% of inhibition. Triacontanol, also, was effective, but its effectivity was lower than that of the M.H.A.A.B.W. at similar doses.

These results shown that M.H.A.A.B.W. is more effective in the granule by cotton model than in the pleuresy by carragenine model. These two experimental models are distinguished in different aspects as are: in the granule by cotton model the most significant thing is the cellular migration (neutrophilic leucocites) while in the pleuresy by carragenine model is the inflamatory exudate (edema by increase of the vascular permeability), this last one effect is closely dependent of prostaglandins (E and F). Of the mediators of the inflamatory process, the leukotrienes, especially the LTB4 shows a potent chemiotactic effect of polimorphonuclear leucocites inducing aggregation, deaggregation and freedom of lisosomal enzymes from them.

As a possible explanation to this fact, is that M.H.A.A.B.W. inhibited, somewhere, the synthesis or liberation of leukotrienes, producing an antiinflamatory action (inhibition of the cellular migration) but also moving the aminoacid metabolism to the formation of primary prostaglandins that mediated in the increase of liquid in the exudate. It means that the effectivity of M.H.A.A.B.W. as an antiinflamatory agent will be useful only in process in which the cellular migration is involved.

EXAMPLE 10

A group of guinea pig albines of both sexes, with an average weight ranging from 280–350 g, were adapted to laboratory conditions for a week with free access to water and food. These animals were anaesthetized with sodium phentobarbital (50 mg/kg) i.p. administered. A canule was inserted in the trachea and conected with a breathing pump (55 breathes/min). Animals were artificially ventilated with a volume of 3–4 mL. The tracheal pressure was determined using a pressure transductor (MP 0.5) concected with a poligraph.

M.H.A.A.B.W., object of the present invention, was administered by endovenous route previous to the administration of PAF (40 ng/kg, i.p.) at doses of 10, 1 and 0.5 mg/kg respectively. In order to determine the effect of M.H.A.A.B.W. over the answer to the histamine induced by PAF, 10 min before the administration of M.H.A.A.B.W. the animals were treated with PAF or with saline solution (controls) later than reproducible answer to histamine (2–12 ug/kg i.v.) were obtained in all cases. In Tables 15 and 16 are shown the obtained results.

TABLE 15

Effect of M.H.A.A.B.W. over the broncoconstriction induced by PAF in guinea pigs

|  | Dose (mg/kg) | % of broncoconstriction maxima |
| --- | --- | --- |
| Controls | — | 39.60 |
| M.H.A.A.B.W. | 1.0 | 13.80* |
| Controls | — | 21.28 |
| M.H.A.A.B.W. | 0.5 | 20.26 n.s. |

*$p < 0.05$ (U de Mann Whitney test)

The maximun precent of broncoconstriction was obtained closing the trachea of each animal at the end of each experiment.

TABLE 16

Effect of M.H.A.A.B.W. over the hiper-answer to the histamine induced by PAF (40 ng/kg) in guinea pigs

| | Doses (mg/kg) | n | Broncoconstriction (%) pre-PAF | post-PAF |
| --- | --- | --- | --- | --- |
| Controls | — | 8 | 100 | 157 +/− 28 |
| M.H.A.A.B.W. | 10 | 6 | 100 | 105 +/− 13** |
| Controls | — | 5 | 100 | 199 +/− 47.6 |
| M.H.A.A.B.W. | 1.0 | 5 | 100 | 117 +/− 25.3** |
| Controls | — | 4 | 100 | 183.25 +/− 18.0 |
| M.H.A.A.B.W. | 0.5 | 4 | 100 | 172.5 +/− 15 n.s. |

**$p < 0.01$ (U de Mann Whitney test)

The answer to histamine, before the administration of PAF, was taken as 100% in each of the animals. M.H.A.A.B.W. provoke changes in the broncoconstrictor answer to histamine, but diminished significantly, both, the broncoconstriction induced by PAF as well as the hiperanswer to the histamine induced by this agent at concentration between 1 and 10 mg/kg.

This M.H.A.A.B.W. shows an effect over receptors to PAF and/or antagonists of leukotrienes and/or inhibitors of lipoxygenase. This effect could explain the antiulcer and antiinflamatory actions previously reported. As can be seen, the new M.H.A.A.B.W., object of the present invention, did not blockade nor increase the broncoconstrictor effect of histamine, that is why is discarded an antihistaminic effect.

EXAMPLE 11

Is done a comparative study between the properties of the natural mixtures of higher primary aliphatic alcohols obtained from bee wax (M.H.A.A.B.W.), object of the present invention, and that of the higher primary aliphatic alcohols obtained from sugar cane wax (EPO 0 488 928) (named M.H.A.A.S.C.W. since this moment). This study permit the possibility of stablishing that both mixtures not only differs in the number of alcohols and in the relative composition of the alcohols present in both of them, but also, in its pharmacological profile, in different experimental models traditionally used in the pharmacological screening, are also different. For that reason are developed the experiments that are described as follows:

a) antiinflamatory effect: In order to corroborate the antiinflamatory effect of both mixtures, the models of pleuresy by carragenine and granule by cotton were used, doses of 100 and 200 mg/kg, respectively, were used.

b) antiulcer effect: In order to corroborate the antiulcer effect of both mixtures it was used the experimental methodology previously described in Example 8 of the present invention, using doses of 25 mg/kg of corporal weight for both mixtures.

c) hipolipidemic effect: Male New Zealand rabbits were used and divided in the following groups a) controls, b) M.H.A.A.B.W. (5 mg/kg) and c) M.H.A.A.S.C.W. (5 mg/kg) administered orally during 1 month. Each 15 days blood samples were taken in order to determine the lipidic parameters (total cholesterol, triglycerides, HDL-C, LDL-C and VLDL-C).

d) antiischemic effect: For the analysis of both mixtures over the cerebral ischemia it was used the model in which cerebral ischemia is provoked in Mongolian gerbils by carotide ligature. Female Mongolian gerbils, of 60 to 80 g of weight, were used that were adapted to laboratory conditions with free access to food and water. Both mixtures were administered by i.p route using for this purposses a suspension in a 2% Tween 20/water vehicle. The animals were distributed in the following experimental groups: 1) control (vehicle 2% Tween 20/water), 2) M.H.A.A.B.W. (200 mg/kg) and 3) M.H.A.A.S.C.W. (200 mg/kg).

The ligature of the left common carotide was done anaesthetizing the animals with an ether atmosphere. The animals were observed for 24 h, registering the appereance of clinical symphtoms of cerebral damage, such as circling, rolling and convulsions, as well as the number of deaths produced during the experiment.

e) antiplatelet aggregation effect: In order to corroborate the effect of both mixtures on the platelet aggregation in rats, induced by ADP or collagen, a number of male Sprague Dawley rats, weighing 250–350 g, were used. Each one of the mixtures was administered orally as a suspension in a acacia gum/water vehicle (1 mL/100 g body weight) for 4 weeks using gastric gavage. The animals were randomly distributed in 3 experimental groupsa) control (only received vehicle), b) M.H.A.A.B.W. (25 mg/kg) and c) M.H.A.A.S.C.W. (25 mg/kg).

For the development of the platelet aggregation assay, the rats were anaesthetized in ether atmosphere. After the abdomen is open, blood was extracted (5 mL) from cava vein and mixed with 3.8% sodium citrate (1 volume of sodium citrate for 9 volumes of blood). The platelet rich plasma (PRP) was obtained by blood centifugation and the platelet poor plasma (PPP) was obtained by centrifugation of PRP aliquots at 330 g for 15 min. Platelet aggregation was induced by ADP or collagen and was registered in a Payton aggregometer.

f) antithrombotic effect: For the study of the antithrombotic effect the venous thrombosis model was used. The following treatments were administered for these purposses: 1) control, 2, 3, 4) M.H.A.A.B.W. (25, 50 and 100 mg/kg), repectively and 5, 6, 7) M.H.A.A.S.C.W. 25, 50 and 100 mg/kg) respectively.

Rats were anaesthetized with sodium phentobarbital (40 mg/kg) by i.p. route. Later on, were injected with hipotonic saline solution (0.22% NaCl) (1 mL/100 g body weight) by the femoral vein. A minute later, the abdomen was opened and the cava vein was exposed, isolated and ligatured passing a thread through the vein. The abdomen was closed, provisionally, for 10 min, later on, it was reopened and the cava vein was ligatured again, 2 cm below the first ligature. Inmediately, it was removed and longitudinal opened, the thrombo was removed and was set in a humid oven at room temperature, being weighed 1 hour later.

The results obtained after the development of all these pharmacological assays are summarized in Table 17.

TABLE 17

Comparative effect between the natural mixture of alcohols obtained from bee wax and those obtained from sugar cane wax

| Assay | M.H.A.A.S.C.W. | M.H.A.A.B.W. |
|---|---|---|
| antiinflamatory | + | − |
| hipolipidemic effect | − | +++ |
| antiischemic | + | +++ |
| antiulcer | +++ | + |
| antiplatetlet aggregation | − | + |
| antithrombotic | − | + | with activity:
(+) discrete
(++) moderated
(+++) higher
(−) without any activity As can be observed, from these results, the pharmacological properties of both natural mixtures of higher primary aliphatic alcohols are differents, only in the antiulcer effect both mixtures exhibit activity, but, as can be shown in the Table, the effect of the mixture of alcohols obtained from bee wax (M.H.A.A.B.W.) is much more effective than that obtained from sugar cane wax (M.H.A.A.S.C.W.).

We claim:

1. The method for the treatment of gastric and duodenal ulcers comprising the administration of a mixture of higher primary aliphatic alcohols obtained from bee wax wherein said mixture of primary aliphatic alcohols comprises 1-tetracosanol 9.0–15.0% (weight)

1-hexacosanol 12.0–18.0%

1-octacosanol 13.0–20.00%

1-triacontanol 20.0–30.00%

1-dotriacontanol 13.0–21.0%

1-tetratriacontanol 1.5–3.5%.

* * * * *